US012676241B2

(12) United States Patent
Wei et al.

(10) Patent No.:  US 12,676,241 B2
(45) Date of Patent:  Jul. 7, 2026

(54) METHOD AND SYSTEM FOR DETERMINING INTRACRANIAL HEMODYNAMIC PARAMETER

(71) Applicant: SHANGHAI UNITED IMAGING HEALTHCARE CO., LTD., Shanghai (CN)

(72) Inventors: Yuan Wei, Shanghai (CN); Xiao-Dong Wang, Shanghai (CN); Jian Guo, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 628 days.

(21) Appl. No.: 18/092,264

(22) Filed: Dec. 31, 2022

(65) Prior Publication Data

US 2023/0215584 A1    Jul. 6, 2023

(30) Foreign Application Priority Data

Dec. 31, 2021    (CN) .......................... 202111674638.X

(51) Int. Cl.
| | |
|---|---|
| *G16H 50/50* | (2018.01) |
| *A61B 5/02* | (2006.01) |
| *A61B 6/50* | (2024.01) |

(52) U.S. Cl.
CPC ......... *G16H 50/50* (2018.01); *A61B 5/02007* (2013.01); *A61B 6/507* (2013.01)

(58) Field of Classification Search
CPC ........ G16H 50/50; G16H 30/40; G16H 50/30;

A61B 5/02; A61B 5/02007; A61B 6/50; A61B 6/507; A61B 5/03; A61B 6/00; A61B 6/03; A61B 5/031; A61B 6/486;
(Continued)

(56) References Cited

U.S. PATENT DOCUMENTS

| | | | | |
|---|---|---|---|---|
| 8,315,812 | B2 * | 11/2012 | Taylor | ................ A61B 5/02007 |
| | | | | 382/128 |
| 10,092,247 | B2 * | 10/2018 | Taylor | .................... G16H 50/50 |
| 10,111,635 | B2 * | 10/2018 | Kato | ....................... A61B 6/507 |

(Continued)

FOREIGN PATENT DOCUMENTS

| | | | | |
|---|---|---|---|---|
| CN | 104036107 | A * | 9/2014 | ............. A61B 6/466 |
| CN | 107122621 | A * | 9/2017 | ............. A61B 34/10 |

(Continued)

OTHER PUBLICATIONS

Solomon, Stephen B., et al. "Real-time bronchoscope tip localization enables three-dimensional CT image guidance for transbronchial needle aspiration in swine." Chest 114.5 (1998): 1405-1410. (Year: 1998).*

(Continued)

*Primary Examiner* — Stephen R Koziol
*Assistant Examiner* — Benedict E Lee

(57) ABSTRACT

A method for determining an intracranial hemodynamic parameter according to embodiments of the present disclosure is provided, which includes determining a three-dimensional a model of a blood vessel based on CT angiographic data, and determining at least one of a boundary condition of each inlet or a boundary condition of each outlet in the three-dimensional vessel model based on CT perfusion imaging data and CT angiographic data.

20 Claims, 5 Drawing Sheets

(58) Field of Classification Search

CPC ......... A61B 6/032; A61B 6/481; A61B 6/504;
A61B 6/5205; A61B 6/5217; A61B 6/52

See application file for complete search history.

(56) References Cited

U.S. PATENT DOCUMENTS

| | | | | |
|---|---|---|---|---|
| 10,278,662 B2 * | 5/2019 | Ishii | ..................... | A61B 6/5217 |
| 10,610,184 B2 * | 4/2020 | Sakaguchi | ........... | A61B 6/5217 |
| 10,658,085 B2 * | 5/2020 | Shim | ..................... | A61B 6/5217 |
| 10,842,446 B2 * | 11/2020 | Ishii | ....................... | A61B 6/488 |
| 10,896,530 B2 * | 1/2021 | Sakaguchi | ............. | A61B 6/032 |
| 11,145,224 B2 * | 10/2021 | Cho | ........................ | A61B 5/026 |
| 11,202,612 B2 * | 12/2021 | Sakaguchi | ........... | A61B 6/5217 |
| 11,490,867 B2 * | 11/2022 | Homann | ................ | A61B 6/486 |
| 11,896,416 B2 * | 2/2024 | Huo | ........................ | A61B 6/507 |
| 12,249,052 B2 * | 3/2025 | Lee | ........................... | G06T 5/77 |
| 2014/0236011 A1 * | 8/2014 | Fan | ..................... | A61B 8/4477 600/407 |
| 2014/0236547 A1 * | 8/2014 | Itu | ......................... | G16H 50/50 703/2 |
| 2016/0070877 A1 * | 3/2016 | Taylor | ................... | G16H 50/50 703/9 |
| 2019/0298291 A1 | 10/2019 | Yang | | |

FOREIGN PATENT DOCUMENTS

| | | | | | |
|---|---|---|---|---|---|
| CN | 107491636 | A | * | 12/2017 | ........... A61B 6/5229 |
| CN | 103995989 | B | * | 11/2018 | |
| CN | 111317455 | A | * | 6/2020 | .............. A61B 8/06 |
| CN | 111357055 | A | * | 6/2020 | ............ G16H 30/40 |
| CN | 113164131 | A | | 7/2021 | |
| EP | 3659505 | A1 | | 6/2020 | |
| WO | WO-2016030744 | A1 | * | 3/2016 | ......... A61B 5/02007 |

OTHER PUBLICATIONS

Chinese Office Action (CN Application No. 202111674638.X) , dated Mar. 27, 2025, 7 pages.

Nie Yu, "Research on the Fractional flow reserve calculation based on CT image three dimensional reconstruction", China Master's Theses Full-text Database, No. 6, Jun. 15, 2018, (75 pages).

Mu, Yue et al., "Coronary Computed Tomography Angiography in Evaluation of Coronary Artery Functional Stenosis", Advances in Cardiovascular Diseases, vol. 42, No. 3, Mar. 25, 2021 (5 pages).

Supplemental Search Report of CN202111674638X, dated Jul. 29, 2025, 3 pages.

* cited by examiner

300

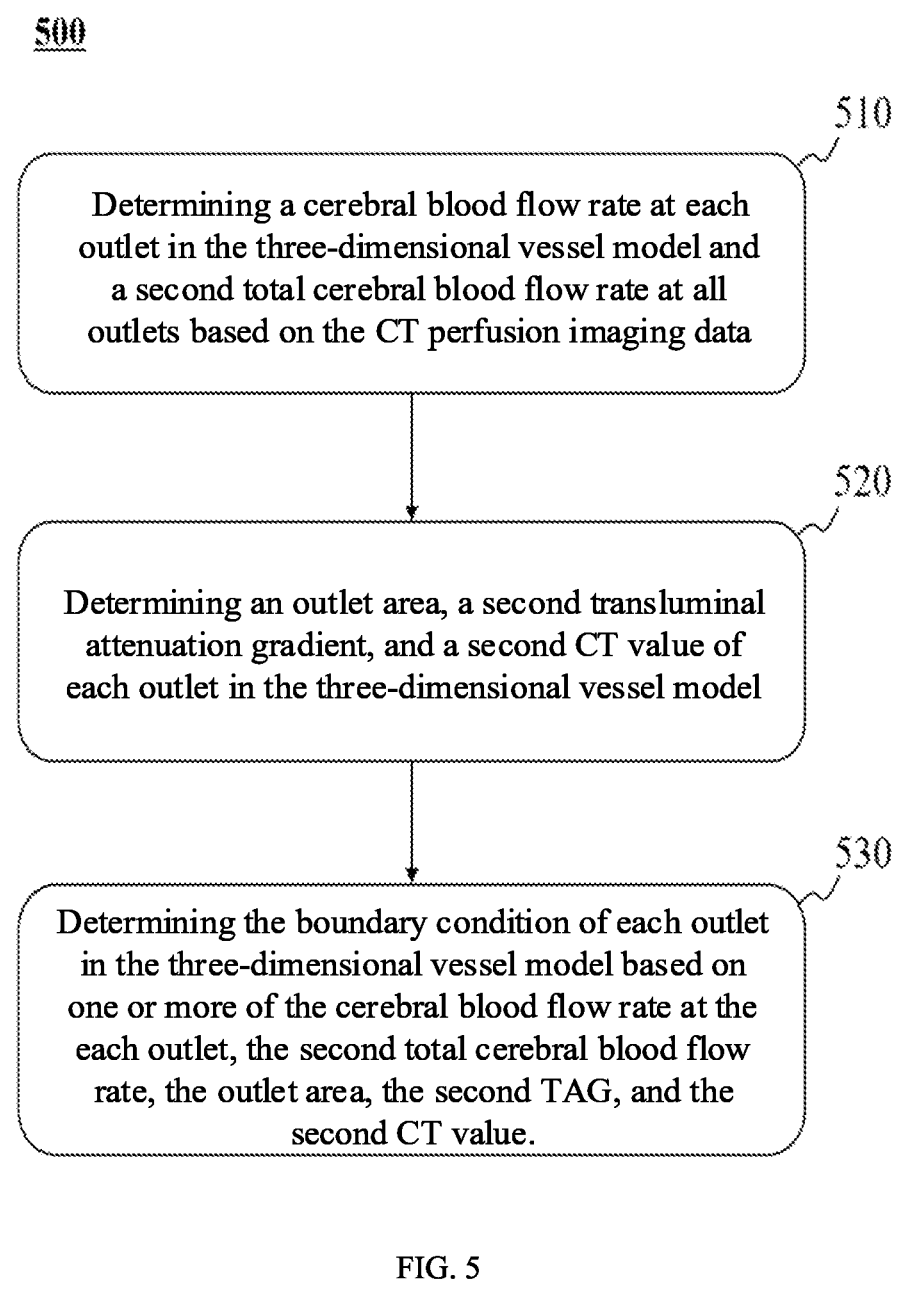

500

510

Determining a cerebral blood flow rate at each outlet in the three-dimensional vessel model and a second total cerebral blood flow rate at all outlets based on the CT perfusion imaging data

520

Determining an outlet area, a second transluminal attenuation gradient, and a second CT value of each outlet in the three-dimensional vessel model

530

Determining the boundary condition of each outlet in the three-dimensional vessel model based on one or more of the cerebral blood flow rate at the each outlet, the second total cerebral blood flow rate, the outlet area, the second TAG, and the second CT value.

FIG. 5

METHOD AND SYSTEM FOR DETERMINING INTRACRANIAL HEMODYNAMIC PARAMETER

CROSS-REFERENCE TO RELATED APPLICATIONS

The present application claims the priority to Chinese Patent Application No. 202111674638.X, filed on Dec. 31, 2021, which is incorporated by reference herein in its entirety.

TECHNICAL FIELD

The present disclosure relates to the field of diagnostic scanning, and particularly to a method and a system for determining an intracranial hemodynamic parameter.

BACKGROUND

Numerous basic and clinical studies have shown that an abnormal hemodynamic environment is an important cause of vascular endothelial cell injury and is closely related to the occurrence of various cardiovascular and cerebrovascular diseases. Therefore, it is of great scientific value and clinical significance to conduct researches on the occurrence, development and treatment of the cerebrovascular diseases from a hemodynamic perspective. By numerical calculations of computational fluid dynamics, hemodynamic parameters such as blood pressure, blood flow velocity, wall shear stress, and oscillatory shear index in the regions of interest of the blood vessels can be determined. However, how to quickly and accurately simulate boundary conditions of inlets and outlets of the blood vessels becomes a constraint that affects the efficiency and effectiveness of the calculations of computational fluid dynamics.

Therefore, it is desired to provide a method and a system for determining an intracranial hemodynamic parameter to determine a boundary condition of an intracranial blood vessel and further determine the intracranial hemodynamic parameter.

SUMMARY

One aspect of the present disclosure provides a method for determining an intracranial hemodynamic parameter, which includes determining a three-dimensional vessel model based on CT angiographic data, and determining at least one of a boundary condition of each inlet or a boundary condition of each outlet in the three-dimensional vessel model based on CT perfusion imaging data and the CT angiographic data.

Another aspect of the present disclosure provides a system for determining an intracranial hemodynamic parameter, which includes a first determination module configured to determine a three-dimensional vessel model based on CT angiography data, and a second determination module configured to determine at least one of a boundary condition of each inlet or a boundary condition of each outlet in the three-dimensional vessel model based on CT perfusion imaging data and the CT angiography data.

Yet another aspect of the present disclosure provides a device for determining an intracranial hemodynamic parameter, which includes a processor and a memory including computer instructions stored thereon. The processor is configured to, when executing the computer instructions, determine a three-dimensional vessel model based on CT angiography data, and determine at least one of a boundary condition of each inlet or a boundary condition of each outlet in the three-dimensional vessel model based on CT perfusion imaging data and the CT angiography data.

Yet another aspect of the present disclosure provides a non-transitory computer-readable storage medium having computer instructions stored thereon. The computer instructions, when executed by a processor, cause the processor to determine a three-dimensional vessel model based on CT angiography data, and determine at least one of a boundary condition of each inlet or a boundary condition of each outlet in the three-dimensional vessel model based on CT perfusion imaging data and the CT angiography data.

BRIEF DESCRIPTION OF THE DRAWINGS

This specification will be further described with exemplary embodiments which will be described in detail by accompanying drawings. These embodiments are not restrictive, and in these embodiments the same reference signs indicate the same structure.

FIG. 5 is an exemplary flow chart illustrating determination of a boundary condition of each outlet in a three-dimensional vessel model, according to some embodiments of the disclosure.

DETAILED DESCRIPTION OF EMBODIMENTS

Figure 1:
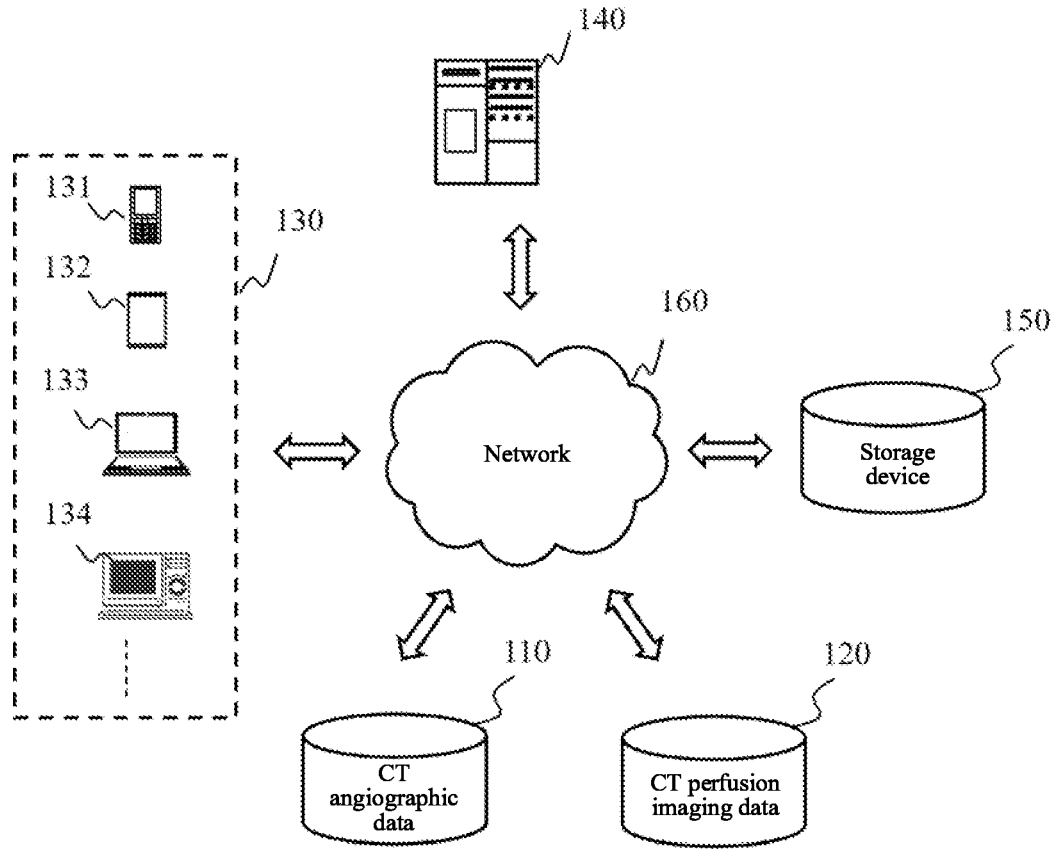
FIG. 1 is a schematic diagram illustrating an application scenario of a system for determining an intracranial hemodynamic parameter, according to some embodiments of the disclosure.

In order to more clearly illustrate the solutions of the embodiments of the present disclosure, a brief description of the accompanying drawings that are required to be used in the description of the embodiments will be given. It will be apparent that the accompanying drawings in the following description are only some examples or embodiments of the present disclosure, and that based on these drawings, the present disclosure can be applied in other similar scenarios by one of ordinary skill in the art without creative effort. Unless obvious from the linguistic context or otherwise noted, the same reference characters in the drawings represents the same structure or operation.

It should be understood that the terms "system", "device", "unit", and/or "module" used herein are intended to distinguish different components, elements, parts, sections, or assemblies of different levels. However, these words may be replaced by other words that realize the same purposes.

The words "first", "second" or the like as used in the specification and the claims of the disclosure are not intended to indicate any order, number, or importance, but are used only to distinguish different components. Similarly, the word "a", "an", "one" or similar words do not constitute a numerical limitation, but refers to at least one element. Unless otherwise noted, similar terms such as "front", "back", "bottom", and/or "top" are used for illustrative purpose only, and are not limited to a certain location or spatial orientation. In general, the terms "include" and "comprise" suggest only inclusion of clearly identified steps or elements that do not constitute an exclusive list, and the method or device may also include other steps or elements.

The flowcharts used in the disclosure illustrate operations that systems implement according to some embodiments in the disclosure. It will be understood that the operations may not necessarily be implemented in sequence. Rather, these operations may be implemented inversely, or implemented simultaneously. Moreover, other operations may be added to the process, or one or more operations may be removed from the process.

FIG. 1 is a schematic diagram illustrating an application scenario of a system for determining an intracranial hemodynamic parameter according to some embodiments of the present disclosure.

The system 100 for determining an intracranial hemodynamic parameter can be used to calculate hemodynamic parameters of intracranial vessels. The hemodynamic parameter includes, but are not limited to, blood pressure, blood flow velocity, blood flow rate, wall shear stress (WSS), or oscillatory shear index (OSI), etc. As shown in FIG. 1, in some embodiments, the application scenario of the system 100 for determining an intracranial hemodynamic parameter may include CT angiographic data 110, CT perfusion imaging data 120, a terminal device 130, a processing device 140, a storage device 150, and a network 160.

The CT angiographic data 110 may refer to the data about a patient's blood vessels obtained by CT angiography techniques. In some embodiments, the CT angiographic data 110 can reflect three-dimensional structural information of the patient's tissues and organs.

The CT perfusion imaging data 120 may refer to data about a patient's blood vessels obtained by CT perfusion imaging techniques. In some embodiments, the CT perfusion imaging data 120 can reflect the blood supply to the patient's tissues and organs.

The terminal device 130 may be any terminal for sending or receiving instructions. The terminal device 130 may communicate with and/or connect to other components of the system 100, for example, the processing device 140. In some embodiments, the terminal device 130 may include, for example, one of a mobile device 131, a tablet computer 132, a laptop computer 133, a desktop computer 134, other devices with input and/or output functions, or any combination thereof. In some embodiments, a user (e.g., a doctor or an operator) may operate the terminal device 130 to send instructions to other components of the system 100.

The processing device 140 may process data and/or information obtained from other devices or various components of the system 100. For example, the processing device 140 may acquire the CT angiographic data 110 and the CT perfusion imaging data 120, and analyze and process them. In some embodiments, the processing device 140 may be a single server or a server group. The server group may be in a centralized manner or in a distributed manner. In some embodiments, the processing device 140 may be local or remote. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or any combination thereof. In some embodiments, the processing device 140 may include one or more processors (e.g., a single-chip processor or a multi-chip processor). In some embodiments, the processing device 140 may be an independent device. In some embodiments, the processing device 140 may be a part of the terminal device 130. For example, the processing device 140 may be integrated within the terminal device 130.

The storage device 150 may store data, instructions, and/or any other information. For example, the storage device 150 may store the CT angiographic data 110 and the CT perfusion imaging data 120. For another example, the storage device 150 may store data obtained from various components of the system 100, e.g., the processing device 140, etc. In some embodiments, the storage device 150 may store data and/or instructions to be performed or used by the processing device 140 to perform the exemplary methods described in the disclosure. In some embodiments, the storage device 150 may include a mass storage, a removable memory, a volatile read-write memory, read-only memory (ROM), etc., or any combination thereof. In some embodiments, the storage device 150 may be implemented on a cloud platform.

The network 160 may connect the components of the system 100 and/or connect the system 100 to external resources. In some embodiments, information and/or data may be exchanged among various components of the system 100 via the network 160. For example, the processing device 140 and the terminal device 130 may be connected or communicate via the network 160. In some embodiments, the network 160 may include at least one network access point. For example, the network 160 may include a wired and/or wireless network access point, such as a base station and/or an internet exchange point, and at least one component of the system 100 may be connected to the network 160 via the access point to exchange data and/or information.

It should be noted that the application scenario of the system 100 for determining an intracranial hemodynamic parameter is provided for illustrative purpose only, and is not intended to limit the scope of the present disclosure. For those of ordinary skill in the art, a variety of modifications or variations may be made in accordance with the description of the present disclosure. For example, the system 100 for determining an intracranial hemodynamic parameter may also include an information source (e.g., a scanning device) providing the CT angiographic data 110 and the CT perfusion imaging data 120. For another example, the system 100 for determining an intracranial hemodynamic parameter may perform similar or different functions on other devices. Nevertheless, these variations and modifications will not depart from the scope of the present disclosure.

Figure 2:
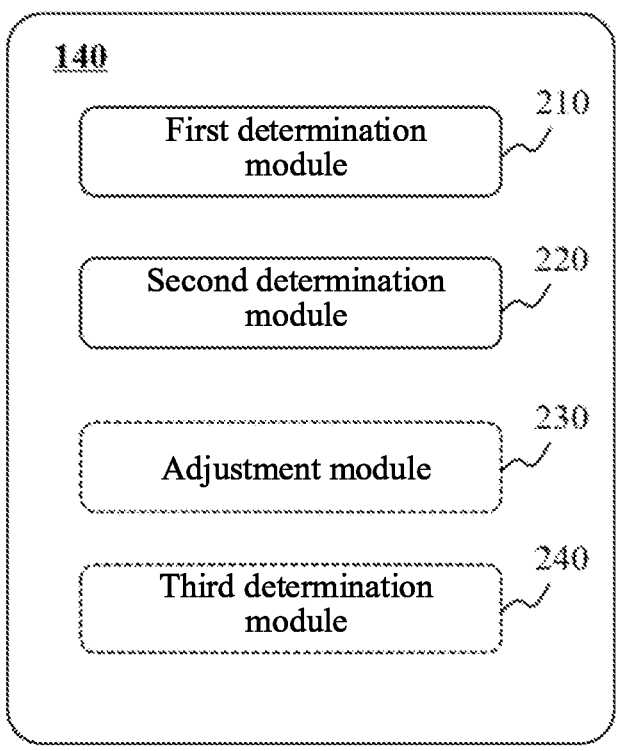
FIG. 2 is an exemplary diagram of a processing device including various modules, according to some embodiments of the disclosure.

FIG. 2 is an exemplary diagram of the processing device including various modules according to some embodiments of the present disclosure.

As shown in FIG. 2, in some embodiments, the processing device 140 may include a first determination module 210 and a second determination module 220.

The first determination module 210 may be configured to determine a three-dimensional vessel model based on the CT angiographic data. More about the CT angiographic data and the three-dimensional vessel model can be found in FIG. 3 and corresponding description thereof, and will not be repeatedly described here.

The second determination module 220 may be configured to determine a boundary condition of each inlet and/or a boundary condition of each outlet in the three-dimensional vessel model based on the CT perfusion imaging data 120 and the CT angiographic data 110. More about the CT perfusion imaging data and the boundary condition of each inlet and/or a boundary condition of each outlet in the three-dimensional vessel model can be found in FIG. 3 and corresponding description thereof, and will not be repeatedly described here.

In some embodiments, the processing device 140 may also include an adjustment module 230 and a third determination module 240.

The adjustment module 230 may be configured to adjust the three-dimensional vessel model based on adjustment parameters to obtain an adjusted three-dimensional vessel model. More about the adjustment parameters and the adjusted three-dimensional vessel model can be found in FIG. 6 and corresponding description thereof, and will not be repeatedly described here.

The third determination module 240 may be configured to determine a hemodynamic parameter of a specified region in the adjusted three-dimensional vessel model based on the adjusted three-dimensional vessel model and boundary conditions corresponding to the adjusted three-dimensional vessel model. More about the boundary conditions corresponding to the adjusted three-dimensional vessel model and the hemodynamic parameter of the specified region in the adjusted three-dimensional vessel model can be found in FIG. 6 and corresponding description thereof, which will not be repeated.

It will be understood that the various modules of the processing device 140 shown in FIG. 2 can be implemented in various ways. For example, in some embodiments, they may be implemented by hardware, software, or a combination of software and hardware. The above description of the various modules of processing device 140 is for descriptive convenience only, but not intended to limit the present disclosure to the exemplary embodiments. It will be understood that, for those skilled in the art, based on fully understanding the principle of the disclosure, it would be possible to make any combination of the individual modules, or form a subsystem to connect other modules without departing from this principle. For example, the functions of the first determination module 210, the second determination module 220, the adjustment module 230 and the third determination module 240 may be realized on the same module, or by multiple modules jointly.

Figure 3:
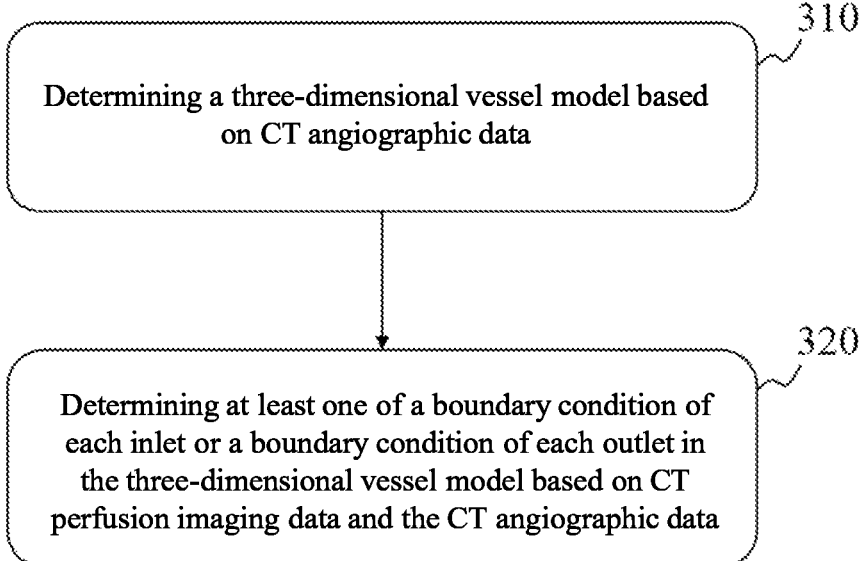
FIG. 3 is a schematic diagram of a method for determining an intracranial hemodynamic parameter, according to some embodiments of the disclosure.

FIG. 3 is a schematic diagram of a method for determining an intracranial hemodynamic parameter according to some embodiments of the disclosure. In some embodiments, a process 300 may be performed by the processing device 140. As shown in FIG. 3, the process 300 includes the following steps 310, 320.

At step 310, a three-dimensional vessel model is determined based on CT angiographic data. In some embodiments, the step 310 may be performed by the first determination module 210.

In some embodiments, a blood vessel of a patient may be modeled based on corresponding CT angiographic data to obtain a three-dimensional vessel model of the blood vessel of the patient. The three-dimensional vessel model may contain at least one inlet and at least one outlet. The inlet may refer to an entrance of blood flow in the three-dimensional vessel model, and the outlet may refer to an exit of blood flow in the three-dimensional vessel model. The three-dimensional vessel model may be a model of a complete cerebral arterial circle including lesions in the patient's skull, or a model of a complete anterior cerebral circulation or posterior cerebral circulation including lesions, or a model of an affected vascular segment including lesions. A format of the three-dimensional vessel model may include, but is not limited to, stl, stp, or igs, etc.

It will be understood that different patients have different physical conditions and health status, and therefore there a difference between the determined three-dimensional vessel models based on the CT angiographic data of the different patients.

At step 320, a boundary condition of each inlet and/or a boundary condition of each outlet in the three-dimensional vessel model are/is determined based on CT perfusion imaging data and the CT angiographic data. In some embodiments, the step 320 may be performed by the second determination module 220.

In some embodiments, the boundary condition of each inlet in the three-dimensional vessel model may include a corrected flow rate at each inlet in the three-dimensional vessel model. More about the corrected flow rate at each inlet can be found in FIG. 4 and corresponding description thereof, and will not be repeatedly described here. In some embodiments, the boundary condition of each outlet of the three-dimensional vessel model may include an arterial viscous resistance, a peripheral resistance, and a compliance of each outlet in the three-dimensional vessel model. More about the arterial viscous resistance, the peripheral resistance, and the compliance of each outlet can be found in FIG. 5 and the corresponding description thereof, and will not be repeatedly described here. In some embodiments, the boundary condition of each inlet and the boundary condition of each outlet in the three-dimensional vessel model may also include other parameters, such as blood pressure at each inlet and each outlet.

In some embodiments, various data analysis algorithms, such as a regression analysis, a discriminant analysis, or the like, may be used to analyze and process the CT perfusion imaging data and the CT angiographic data to determine the boundary condition of each inlet and/or the boundary condition of each outlet in the three-dimensional vessel model.

In some embodiments, the angiographic information of each inlet in the three-dimensional vessel model can be determined based on the CT angiographic data. The angiographic information of each inlet includes a first transluminal attenuation gradient (TAG) and/or a first CT value of the each inlet in the three-dimensional vessel model. A first total cerebral blood flow rate at all the inlets in the three-dimensional vessel model is determined based on the CT perfusion imaging data. The boundary condition of each inlet in the three-dimensional vessel model is determined based on the angiographic information of the each inlet and the first total cerebral blood flow rate. More about the embodiment of determining the boundary condition of each inlet in the three-dimensional vessel model can be found in FIG. 4 and corresponding description thereof, and will not be repeatedly described here.

In some embodiments, a cerebral blood flow rate at each outlet in the three-dimensional vessel model and a second total cerebral blood flow rate at all the outlets can be determined based on the CT perfusion imaging data. An outlet area, a second TAG, and a second CT value of each outlet in the three-dimensional vessel model can be determined based on the CT angiographic data. The boundary condition of each outlet in the three-dimensional vessel model can be determined based on one or more of the cerebral blood flow rate at the each outlet, the second total cerebral blood flow rate, the outlet area of the each outlet, the second TAG of the each outlet, and the second CT value of the each outlet. More about the boundary condition of each outlet in the three-dimensional vessel model can be found in FIG. 5 and corresponding description thereof, and will not be repeatedly described here.

In some embodiments, the hemodynamic parameter corresponding to the three-dimensional vessel model may be determined based on the three-dimensional vessel model and the boundary condition of each inlet and the boundary condition of each outlet in the three-dimensional vessel model. For example, when the three-dimensional vessel model is a three-dimensional model of an intracranial vessel, an intracranial hemodynamic parameter may be determined based on the three-dimensional vessel model and the boundary condition of each inlet and the boundary condition of each outlet in the three-dimensional vessel model.

In some embodiments, the three-dimensional vessel model may be meshed based on a computational fluid dynamics solver to obtain a three-dimensional vessel model divided into different meshes. The computational fluid dynamics solver can determine the corresponding hemodynamic parameter of the three-dimensional vessel model based on the boundary condition of each inlet and the boundary condition of each outlet in the three-dimensional vessel model. The computational fluid dynamics solver may be obtained in various ways, for example, it may be obtained through a network. In some embodiments, the meshes may be structured or unstructured ones. In some embodiments, it may also be determined to perform a boundary layer mesh or not. In some embodiments, the meshes at some locations in the three-dimensional vessel model may be encrypted. For example, the meshes at the lesion regions in the three-dimensional vessel model can be encrypted to obtain more detailed information about the hemodynamic parameters of the regions.

Figure 4:
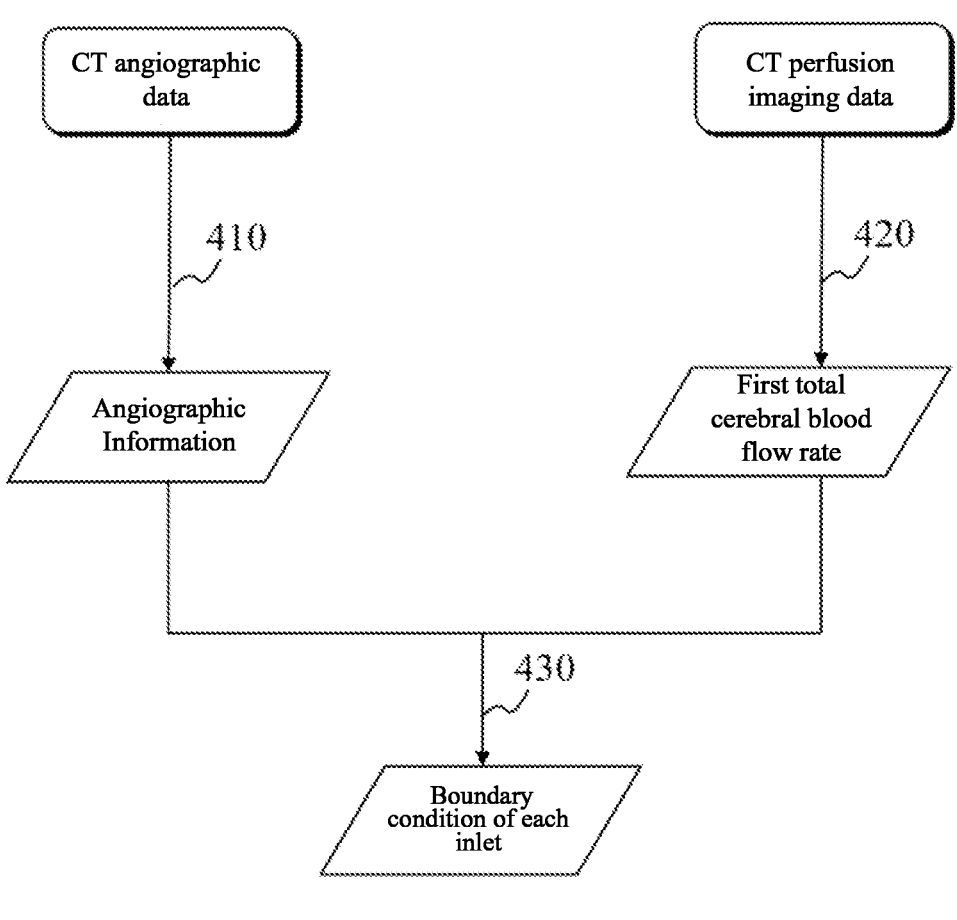
FIG. 4 is a schematic diagram illustrating determination of a boundary condition of each inlet in a three-dimensional vessel model, according to some embodiments of the disclosure.

FIG. 4 is a schematic diagram illustrating determination of the boundary condition of each inlet in the three-dimensional vessel model according to some embodiments of the disclosure. In some embodiments, a process 400 may be performed by the second determination module 220. As shown in FIG. 4, the process 400 includes the following steps 410 to 430.

At step 410, angiographic information of each inlet in the three-dimensional vessel model can be determined based on the CT angiographic data. The angiographic information of each inlet includes the first TAG and/or the first CT value of the each inlet in the three-dimensional vessel model.

The angiographic information of each inlet may refer to information related to the each inlet in the three-dimensional vessel model obtained based on the CT angiographic data. In some embodiments, the angiographic information of each inlet may include the first TAG and/or the first CT value of the each inlet in the three-dimensional vessel model.

The first TAG may refer to the TAG of each inlet in the three-dimensional vessel model. TAG is a linear regression coefficient between a transluminal attenuation and an opening-to-end length of an artery. TAG can be different at different locations of the vessel. In some embodiments, the first TAG may be obtained from the CT angiographic data.

The first CT value may refer to the CT value of each inlet in the three-dimensional vessel model. The CT value can determine the density magnitude of a local tissue or organ in a human body. In some embodiments, the first CT value may be obtained from the CT angiographic data. For example, a CT value of 32 HU is obtained from the CT angiographic data for an inlet in the three-dimensional vessel model.

At step 420, a first total cerebral blood flow rate at all the inlets in the three-dimensional vessel model is determined based on the CT perfusion imaging data.

The first total cerebral blood flow rate may refer to a sum of the cerebral blood flow rates at all the inlets in the three-dimensional vessel model. In some embodiments, the first total cerebral blood flow rate may be obtained from the CT perfusion imaging data. Perfusion parameters of the three-dimensional vessel model may be determined based on the CT perfusion imaging data. The perfusion parameters may include, but are not limited to, cerebral blood flow rate (CBF), local cerebral blood volume (CBV), etc. The cerebral blood flow rate may include a set of values reflecting cerebral blood flow rates at different time points during one cardiac cycle of the vessel, and the local cerebral blood volume may include values of cerebral blood volume in a region of interest (ROI) at different time points during one cardiac cycle. When multiple ROIs exist, there may be multiple sets of values of the local cerebral blood volume. The ROI of the three-dimensional vessel model can be the inlet or outlet of the three-dimensional vessel model. The ROI can be pre-selected by a user. When the three-dimensional vessel model is a model of a complete cerebral arterial circle, the corresponding ROIs can be selected at the bilateral internal carotid arteries and the vertebrobasilar arteries. When the three-dimensional vessel model is a model of a complete anterior or posterior cerebral circle, the corresponding ROIs can be selected at the bilateral internal carotid arteries or the vertebrobasilar arteries, respectively. When the three-dimensional vessel model is an affected vascular segment, the corresponding ROIs can be selected at the start of the vascular segment. When the selected ROIs are the inlets in the three-dimensional vessel model, the cerebral blood flow rate at each inlet can be obtained, and thus the first total cerebral blood flow rate can be obtained. Similarly, when the selected ROIs are the outlets in the three-dimensional vessel model, the cerebral blood flow rate at each outlet can be obtained, and thus the second total cerebral blood flow rate can be obtained. More about the second total cerebral blood flow rate can be found in FIG. 5 and the corresponding description thereof, and will not be repeatedly described here.

When only one inlet is present in the three-dimensional vessel model, a cerebral blood flow rate curve during one cardiac cycle for the only inlet can be calculated and obtained directly based on time-density curve. When there are two or more inlets in the three-dimensional vessel model, the cerebral blood flow rate curve of each inlet calculated and obtained based on the time-density curve needs to be corrected to obtain a corrected flow rate curve of each inlet. Both the cerebral blood flow rate curve and the corrected flow rate curve can reflect the cerebral blood flow rates corresponding to a ROI at different time points within one cardiac cycle. The corrected flow rate may refer to the cerebral blood flow rate obtained by correcting the cerebral blood flow rate of the ROI in the three-dimensional vessel model. Exemplarily, the corrected flow rate at each inlet may refer to the cerebral blood flow rate obtained by correcting the cerebral blood flow rate at each inlet in the three-dimensional vessel model.

At step 430, a boundary condition of each inlet in the three-dimensional vessel model is determined based on the angiographic information of the each inlet in the three-dimensional vessel model and the first total cerebral blood flow rate.

In some embodiments, various data analysis algorithms may be used to process the angiographic information of each inlet in the three-dimensional vessel model and the first total cerebral blood flow rate to determine the boundary condition of each inlet in the three-dimensional vessel model.

In some embodiments, a corrected flow rate at each inlet in the three-dimensional vessel model can be determined based on the first total cerebral blood flow rate and a ratio of a first TAG corresponding to the each inlet to a total inlet TAG. The total inlet TAG may refer to a sum of the first TAGs of all the inlets in the three-dimensional vessel model.

In some embodiments, the corrected flow rate at each inlet in the three-dimensional vessel model can be determined according to equation (1):

$$\frac{\Delta Q_i}{\sum_i^n Q_i} = \frac{Tag_i}{\sum_i^n Tag_i} \tag{1}$$

where $\Delta Q_i$ is the corrected flow rate at the i-th inlet in the three-dimensional vessel model at a time point within one cardiac cycle;

$$\sum_i^n Q_i$$

is the first total cerebral blood flow rate of the three-dimensional vessel model at that time point; $Tag_i$ is the first transluminal density attenuation gradient of the i-th inlet in the three-dimensional vessel model;

$$\sum_i^n Tag_i$$

is the total inlet TAG of the three-dimensional vessel model at that time point; and n is the total number of the inlets in the three-dimensional vessel model.

In some embodiments, the corrected flow rate at each inlet in the three-dimensional vessel model can also be determined according to equation (2):

$$\frac{\Delta Q_i}{\sum_i^n Q_i} = \alpha_1 \frac{Tag_i}{\sum_i^n Tag_i} + \beta_1 \tag{2}$$

where the denotations of $\Delta Q_i$, $$\sum_i^n Q_i,$$

$Tag_i$, $$\sum_i^n Tag_i$$

and n have been described in equation (1), and will not be repeatedly described here; and $\alpha 1$ and $\beta 1$ are correction coefficients for correcting the cerebral blood flow rate at each inlet based on the TAG, and can be predetermined.

In some embodiments, a corrected flow rate at each inlet in the three-dimensional vessel model may also be determined based on the first total cerebral blood flow rate and a ratio of the first CT value corresponding to the each inlet to a total CT value. The total CT value may refer to a sum of the first CT values of all the inlets in the three-dimensional vessel model. In some embodiments, the corrected flow rate at each inlet in the three-dimensional vessel model can be determined according to equation (3):

$$\frac{\Delta Q_i}{\sum_i^n Q_i} = \frac{CT_i}{\sum_i^n CT_i} \tag{3}$$

where the denotations of $\Delta Q_i$, $$\sum_i^n Q_i,$$

and n have been described in equation (1), and will not be repeatedly described here; $CT_i$ is the first CT value of the i-th inlet in the three-dimensional vessel model; and $$\sum_i^n CT_i$$

is the total CT value of all the inlets in the three-dimensional vessel model at that time point.

In some embodiments, the corrected flow rate at inlets of the three-dimensional vessel model can also be determined according to equation (4):

$$\frac{\Delta Q_i}{\sum_i^n Q_i} = \omega_1 \frac{CT_i}{\sum_i^n CT_i} + \beta_2 \tag{4}$$

where the denotations of $\Delta Q_i$, $$\sum_i^n Q_i,$$

$CT_i$, $$\sum_i^n CT_i$$

and n have been described in equation (1) and equation (3), and will not be repeatedly described here; $\omega_1$, $\beta_2$ are correction coefficients for correcting the cerebral blood flow rate at each inlet based on the CT value, and can be predetermined.

In some embodiments, a corrected flow rate at each inlet in the three-dimensional vessel model is determined based on the ratio of the first TAG corresponding to the each inlet to the total inlet TAG, the ratio of the first CT value corresponding to the each inlet to the total CT value, and the first total cerebral blood flow rate. In some embodiments, the corrected flow rate at each inlet in the three-dimensional vessel model can also be determined according to equation (5):

$$\frac{\Delta Q_i}{\sum_i^n Q_i} = \alpha_2 \frac{Tag_i}{\sum_i^n Tag_i} + \omega_2 \frac{CT_i}{\sum_i^n CT_i} + \beta_3 \tag{5}$$

where the denotations of $\Delta Q_i$, $$\sum_i^n Q_i,$$

$Tag_i$, $$\sum_i^n Tag_i,$$

$CT_i$, $$\sum_i^n CT_i$$

and n have been described in equation (1) and equation (3), and will not be repeatedly described here; $\alpha_2$, $\omega_2$ and $\beta_3$ are correction coefficients for correcting the cerebral blood flow rate at each inlet based on the TAG and the CT value, and can be predetermined.

In some embodiments, the corrected flow rate at each inlet may also be determined in other ways. For example, a corresponding correction coefficient is determined based on the first TAG, and a corrected flow rate at each inlet is determined by correcting the cerebral blood flow rate at the each inlet based on the correction coefficient. The correction coefficient corresponding to the first TAG may be determined based on a predetermined correspondence. For example, if the first TAG of an inlet in the three-dimensional vessel model is −7.6 HU/10 mm, the correction coefficient corresponding to this first TAG is 1.1, and the cerebral blood flow rate at this inlet is 20 ml/100 g, then a corrected flow rate of 22 ml/100 g at this inlet can be determined.

FIG. 5 is an exemplary flow chart illustrating determination of the boundary condition of each outlet in the three-dimensional vessel model according to some embodiments of the disclosure. In some embodiments, a process 500 may be performed by the second determination module 220. As shown in FIG. 5, the process 500 includes the following steps 510-530.

At step 510, a cerebral blood flow rate at each outlet in the three-dimensional vessel model and a second total cerebral blood flow rate at all outlets are determined based on the CT perfusion imaging data.

The second total cerebral blood flow rate may refer to a sum of the cerebral blood flow rates at all the outlets in the three-dimensional vessel model. More about the determination of the cerebral blood flow rate at each outlet and the second total cerebral blood flow rate at all the outlets based on the CT perfusion imaging data can be found in FIG. 4 and corresponding description thereof, and will not be repeatedly described here.

At step 520, an outlet area, a second TAG, and a second CT value of each outlet in the three-dimensional vessel model are determined.

The second TAG may refer to a TAG of each outlet in the three-dimensional vessel model. The second CT value may refer to a CT value of each outlet in the three-dimensional vessel model. The second TAG and the second CT value can be obtained directly from the CT angiographic data. The outlet area of each outlet may be determined based on the three-dimensional vessel model.

At step 530, the boundary condition of each outlet in the three-dimensional vessel model is determined based on one or more of the cerebral blood flow rate at the each outlet, the second total cerebral blood flow rate, the outlet area, the second TAG, and the second CT value. In some embodiments, the boundary condition of each outlet in the three-dimensional vessel model may be determined by analysis and calculation based on the one or more of the cerebral blood flow rate at each outlet, the second total cerebral blood flow rate, the outlet area, the second TAG, and the second CT value.

In some embodiments, a compliance of each outlet in the three-dimensional vessel model may be determined based on the ratio of the cerebral blood flow rate corresponding to the each outlet to the second total cerebral blood flow rate and a total outlet compliance. The total outlet compliance is a sum of the compliances of all the outlets in the three-dimensional vessel model. In some embodiments, the total outlet compliance can be calculated according to equation (6):

$$C_{total} = \gamma \frac{Q_{max} - Q_{min}}{P_{max} - P_{min}} \tag{6}$$

where $Q_{max}$ and $Q_{min}$ are a sum of wave crest values of the corrected flow rate curves of all the inlets in the three-dimensional vessel model during one cardiac cycle, and a sum of wave trough values of the corrected flow curves of all the inlets in the three-dimensional vessel model during the cardiac cycle, respectively; $P_{max}$ and $P_{min}$ are a systolic blood pressure and a diastolic blood pressure, respectively, obtained by measuring the blood pressure of the patient; $\gamma$ is a first adjustment coefficient which can be predetermined; $C_{total}$ is the total outlet compliance.

In some embodiments, the total outlet compliance may also be determined by other methods.

In some embodiments, the compliance of each outlet in the three-dimensional vessel model can be determined according to equation (7):

$$C_k = \delta \left( \frac{Q_k}{\sum_k^m Q_k} \right)^{-1} C_{total} \tag{7}$$

where $C_k$ is the compliance of the k-th outlet in the three-dimensional vessel model; $Q_k$ is the cerebral blood flow rate at the k-th outlet in the three-dimensional vessel model;

$$\sum_k^m Q_k$$

is the second total cerebral blood flow rate; $C_{total}$ is the total outlet compliance; m is the total number of outlets in the three-dimensional vessel model; and $\delta$ is a second adjustment coefficient which can be predetermined.

In some embodiments, the compliance of each outlet in the three-dimensional vessel model may also be determined based on a ratio of the outlet area of the each outlet in the three-dimensional vessel model to a total outlet area, a ratio of the cerebral blood flow rate at the each outlet to the second total cerebral blood flow rate, a ratio of the second CT value of the each outlet to a sum of the second CT values of all the outlets, and a ratio of the second TAG of the each outlet to the total outlet TAG. The total outlet TAG may be a sum of the second TAGs of all the outlets, and the total outlet area may be a sum of the outlet areas of all the outlets. In some embodiments, the compliance of each outlet can also be determined according to equation (8):

$$C_k = \left[ \left( \epsilon \left( \frac{A_k}{\sum_k^m A_k} \right)^{-1} + \theta \left( \frac{Q_k}{\sum_k^m Q_k} \right)^{-1} + \vartheta \left( \frac{Tag_k}{\sum_k^m Tag_k} \right)^{-1} + \alpha \left( \frac{CT_k}{\sum_k^m CT_k} \right)^{-1} \right] C_{total} \tag{8}$$

where the denotations of $C_k$, $Q_k$, $$\sum_k^m Q_k,$$

$C_{total}$, and m have been described in equation (7) and will not be repeatedly described here; $A_k$ is the outlet area of the k-th outlet in the three-dimensional vessel model;

$$\sum_k^m A_k$$

is the total outlet area; $Tag_k$ is the second TAG of the k-th outlet in the three-dimensional vessel model;

$$\sum_k^m Tag_k$$

is the total outlet TAG; $CT_k$ is the second CT value of the k-th outlet in the three-dimensional vessel model;

$$\sum_k^m CT_k$$

is a sum of the second CT values of all the outlets; $\epsilon$, $\theta$, $\vartheta$ and $\alpha$ are a third adjustment coefficient, a fourth adjustment coefficient, a fifth adjustment coefficient and a sixth adjustment coefficient respectively, and can be predetermined.

In some embodiments, the compliance of each outlet in the three-dimensional vessel model may also be determined based on one or more of the ratio of the outlet area of the each outlet in the three-dimensional vessel model to the total outlet area, the ratio of the cerebral blood flow rate at the each outlet to the second total cerebral blood flow rate, the ratio of the second CT value of the each outlet to the sum of the second CT values of all the outlets, and the ratio of the second TAG of the each outlet to the total outlet TAG. In this case, the elements included in equation (8) can be removed, or the corresponding adjustment coefficients can be adjusted. For example, when the compliance of each outlet in the three-dimensional vessel model is determined based on the ratio of the outlet area of the each outlet to the total outlet area and the ratio of the cerebral blood flow rate at the each outlet to the second total cerebral blood flow rate, equation (8) can be adjusted to obtain equation (9):

$$C_k = \left[ \epsilon_1 \left( \frac{A_k}{\sum_k^m A_k} \right)^{-1} + \theta_1 \left( \frac{Q_k}{\sum_k^m Q_k} \right)^{-1} \right] C_{total} \tag{9}$$

where the denotations of $C_k$, $Q_k$, $$\sum_k^m Q_k,$$

$C_{total}$, $A_k$, $$\sum_k^m A_k$$

and m have been described in equation (7) and equation (8), and will not be repeatedly described here; $\epsilon_1$ and $\theta_1$ are an adjusted third adjustment coefficient and an fourth adjustment coefficient, respectively, which can be predetermined.

In some embodiments, an outlet resistance value of each outlet in the three-dimensional vessel model may be determined based on a total outlet resistance value and the ratio of cerebral blood flow rate corresponding to the each outlet to the second total cerebral blood flow rate. The total outlet resistance value may be a sum of the outlet resistance values of all the outlets in the three-dimensional vessel model. In some embodiments, the total outlet resistance value may be determined according to equation (10):

$$R_{total} = \frac{P_{mean}}{Q_{mean}} \tag{10}$$

where $R_{total}$ is the total outlet resistance value; $P_{mean}$ is a mean value of the patient's blood pressures, which can be obtained by averaging the measured blood pressures of the patient; $Q_{mean}$ is a mean cerebral blood flow rate at all the inlets in the three-dimensional vessel model, which can be determined based on the first total cerebral blood flow rate and the number of the inlets in the three-dimensional vessel model.

In some embodiments, the outlet resistance value of each outlet can be determined according to equation (11)

$$R_k = \mu \left( \frac{Q_k}{\sum_k^m Q_k} \right)^{-1} R_{total} \tag{11}$$

where the denotations of $Q_k$, $$\sum_k^m Q_k$$

and $R_{total}$ have been described in equation (9) and equation (10); $R_k$ is the outlet resistance value of the k-th outlet in the three-dimensional vessel model; and $\mu$ is a sixth adjustment coefficient which can be predetermined.

In some embodiments, the outlet resistance value of each outlet in the three-dimensional vessel model may also be determined based on the ratio of the outlet area of the each outlet in the three-dimensional vessel model to the total outlet area, the ratio of the cerebral blood flow rate at the each outlet to the second total cerebral blood flow rate, the ratio of the second CT value of the each outlet to the sum of the second CT values of all the outlets, and the ratio of the second TAG of the each outlet to the total outlet TAG. In some embodiments, the outlet resistance value of each outlet may also be determined according to equation (12):

$$R_k =$$

$$\left( \rho \left( \frac{A_k}{\sum_k^m A_k} \right)^{-1} + \sigma \left( \frac{Q_k}{\sum_k^m Q_k} \right)^{-1} + \tau \left( \frac{Tag_k}{\sum_k^m Tag_k} \right)^{-1} + b \left( \frac{CT_k}{\sum_k^m CT_k} \right)^{-1} \right) \qquad (12)$$

$$R_{total}$$

where the denotations of $R_k$, $C_k$, $Q_k$, $$\sum_k^m Q_k,$$

$C_{total}$, $A_k$, $$\sum_k^m A_k,$$

$Tag_k$, $$\sum_k^m Tag_k,$$

$CT_k$, $$\sum_k^m CT_k,$$

$R_{total}$ and m have been described in previous equations, and will not be repeatedly described here; ρ, σ, τ, and b are a seventh adjustment coefficient, an eighth adjustment coefficient, a ninth adjustment coefficient and a tenth adjustment coefficient, respectively, which can be predetermined.

In some embodiments, an outlet resistance value of each outlet in the three-dimensional vessel model may also be determined based on one or more of the ratio of the outlet area of the each outlet to the total outlet area, the ratio of the cerebral blood flow rate at the each outlet to the second total cerebral blood flow rate, the ratio of the second CT value of the each outlet to the sum of the second CT values of all the outlets, and the ratio of the second TAG of the each outlet to the total outlet TAG. In this case, the elements included in equation (12) can be removed, or the corresponding adjustment coefficients can be adjusted. For example, When the outlet resistance value of each outlet is determined based on the ratio of the cerebral blood flow rate at the each outlet to the second total cerebral blood flow rate and the ratio of the second TAG of the each outlet to the total outlet TAG, equation (12) can be adjusted to obtain equation (13):

$$R_k = \left( \sigma_1 \left( \frac{Q_k}{\sum_k^m Q_k} \right)^{-1} + \tau_1 \left( \frac{Tag_k}{\sum_k^m Tag_k} \right)^{-1} \right) R_{total} \qquad (13)$$

where $\sigma_1$ and $\tau_1$ are an adjusted eighth adjustment coefficient and an adjusted ninth adjustment coefficient, respectively, which can be predetermined; and the other elements in equation (13) have been described previously and will not be repeatedly described here.

In some embodiments, an arterial viscous resistance and a peripheral resistance of each outlet in the three-dimensional vessel model are determined based on the outlet resistance value of the each outlet in the three-dimensional vessel model.

The outlet resistance value of each outlet in the three-dimensional vessel model may be a sum of the arterial viscous resistance and the peripheral resistance of the each outlet. In some embodiments, there is a proportional relationship between the arterial viscous resistance and the peripheral resistance, and the arterial viscous resistance and the peripheral resistance of each outlet can be determined according to equation (14):

$$R_p : R_d = \varphi \qquad (14)$$

where $R_p$ is the arterial viscous resistance of an outlet in the three-dimensional vessel model; $R_d$ is the peripheral resistance of the outlet; and φ is a preset ratio which can be predetermined.

Figure 6:
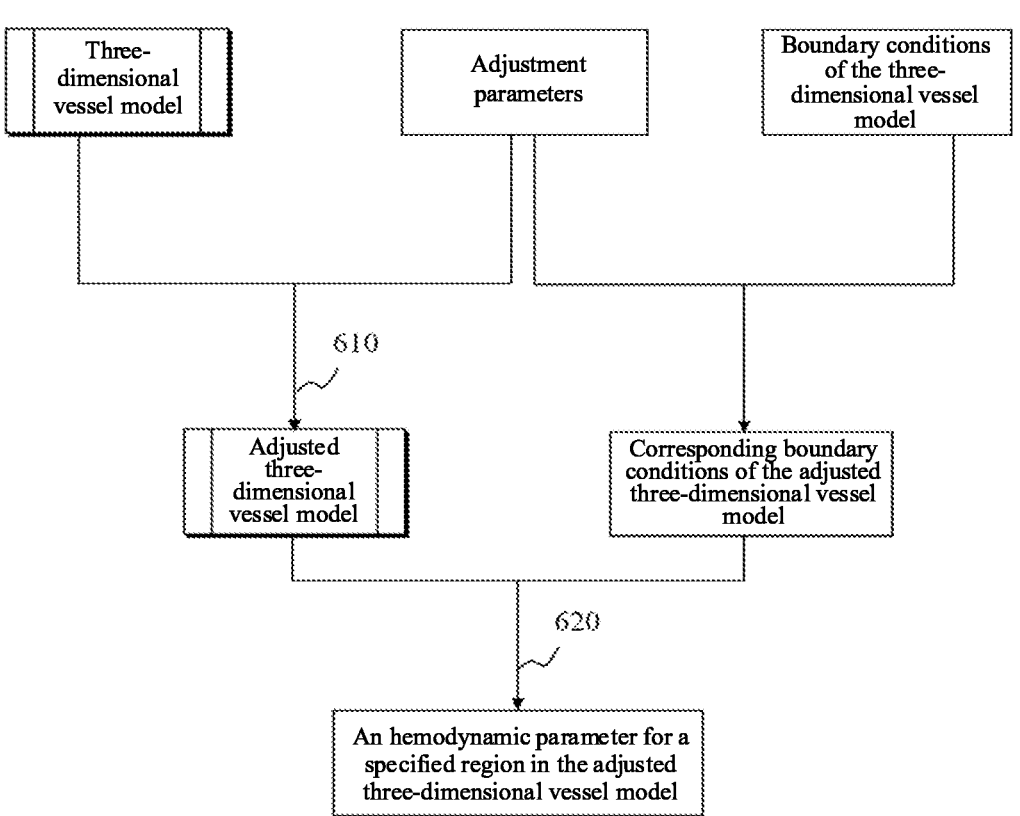
FIG. 6 is a schematic diagram illustrating determination of a hemodynamic parameter of a specified region in an adjusted three-dimensional vessel model, according to some embodiments of the disclosure.

FIG. 6 is a schematic diagram illustrating determination of a hemodynamic parameter for a specified region in an adjusted three-dimensional vessel model, according to some embodiments of the disclosure. In some embodiments, a process 600 may be performed by the processing device 140. As shown in FIG. 6, the process 600 includes the following steps 610, 620.

At step 610, the three-dimensional vessel model is adjusted based on the adjusted parameters to obtain the adjusted three-dimensional vessel model. In some embodiments, step 610 may be performed by an adjustment module 230.

In some embodiments, morphological parameters of the three-dimensional vessel model may be adjusted based on the adjustment parameters to obtain the adjusted three-dimensional vessel model. The morphological parameters may refer to parameters representing the morphology of the three-dimensional vessel model. The adjustment parameters may refer to preset parameters for adjusting the three-dimensional vessel model, which may be predetermined by a user.

At step 620, the hemodynamic parameter for the specified region in the adjusted three-dimensional vessel model is determined based on the adjusted three-dimensional vessel model and corresponding boundary conditions thereof. In some embodiments, step 620 may be performed by a third determination module 240.

In some embodiments, the boundary conditions corresponding to the adjusted three-dimensional model may be determined based on the adjustment parameters. The boundary conditions corresponding to the adjusted three-dimensional vessel model may include the boundary conditions of each inlet and the boundary condition of each outlet in the adjusted three-dimensional vessel model. The boundary conditions corresponding to the adjusted three-dimensional vessel model can be determined based on the boundary conditions corresponding to the three-dimensional vessel model, adjustment parameters, as well as the preset adjustment relationship between the adjustment parameters and the boundary conditions. The boundary conditions corresponding to the three-dimensional vessel model can include the boundary condition of each inlet in the three-dimensional vessel model and the boundary condition of each outlet in the three-dimensional vessel model.

In some embodiments, the adjusted three-dimensional vessel model may be meshed, and the meshes and the boundary conditions corresponding to the adjusted three-dimensional vessel model may be input into a computational fluid dynamics solver to determine a hemodynamic parameter corresponding to each mesh point, thereby determining the hemodynamic parameter for the specified region of the blood vessel corresponding to the adjusted three-dimensional vessel model. For example, a hemodynamic parameter of the lesion regions in the blood vessel corresponding to the adjusted three-dimensional vessel model can be determined. For another example, overall hemodynamic parameters of the blood vessels corresponding to the adjusted three-dimensional vessel model may be determined.

Some embodiments of the present disclosure also disclose a device for determining an intracranial hemodynamic parameter, which includes a processor and a memory. The memory has computer instructions stored thereon. The processor is configured to, when executing the computer instructions, perform the methods for determining an intracranial hemodynamic parameter according the various embodiments of the disclosure described above.

In an embodiment, the processor, when executing the computer instructions, is configured to: determine a three-dimensional vessel model based on CT angiographic data, and determine at least one of a boundary condition of each inlet or a boundary condition of each outlet in the three-dimensional vessel model based on CT perfusion imaging data and the CT angiographic data.

Some embodiments of the present disclosure also disclose a non-transitory computer-readable storage medium that stores computer instructions. When a processor executes the computer instructions in the storage medium, the processor performs the methods for determining the intracranial hemodynamic parameter according the various embodiments of the disclosure as described above.

In an embodiment, when the processor executes the computer instructions, the processor is configured to: determine a three-dimensional vessel model based on CT angiographic data, and determine at least one of a boundary condition of each inlet or a boundary condition of each outlet in the three-dimensional vessel model based on CT perfusion imaging data and the CT angiographic data.

It will be appreciated that, the processor is also configured to, when executing the computer instructions, perform other steps or operations in the methods for determining an intracranial hemodynamic parameter according to various embodiments of the disclosure. These steps or operations have been described in detail above, and therefore will not be repeatedly described here.

Beneficial effects achieved by the embodiments of the present disclosure include, but are not limited to: 1. accurately, quickly, and efficiently determining the boundary condition of each inlet and/or the boundary condition of each outlet of the three-dimensional vessel model by calculation and processing based on the CT angiographic data and the CT perfusion imaging data, thereby determining the hemodynamic parameter of the blood vessels in a non-invasive manner; 2. correcting, by using the first transluminal attenuation gradient obtained based on the CT angiographic data, the flow rate curve obtained based on the CT perfusion imaging data to obtain the corrected flow rate curve, and performing computational fluid dynamics calculations more accurately based on the corrected flow rate curve without repeated iterations; 3. obtaining the hemodynamic parameter of the patient's lesion regions during different lesion periods (e.g., during lesion formation, lesion development and lesion release, etc.) by adjusting the three-dimensional vessel model, for analysis and processing.

It is to be noted that the description of each of the above processes is exemplary and illustrative, but not intend to limit the scope of an application of the disclosure. For those skilled in the art, various modifications and variations can be made to the processes under the teaching of the disclosure, and these modifications and variations remain within the scope of the disclosure.

The basic concepts have been described above, and it is obvious for those skilled in the art that the above disclosure is just exemplary, but not intended to constitute a limitation on the disclosure. Although not expressly stated herein, various modifications, improvements and amendments may be made for the disclosure by those skilled in the art. Such modifications, improvements, and amendments are intended to be suggested by the disclosure, so such modifications, improvements, and amendments remain within the spirit and scope of the exemplary embodiments of the disclosure.

Moreover, specific terminologies have been used to describe embodiments of the present disclosure. For example, the terms "one embodiment", "an embodiment," and/or "some embodiments" mean that a particular feature, structure or characteristic described in connection with the embodiment is included in at least one embodiment of the present disclosure. Therefore, it should be emphasized and noted that "an embodiment", "one embodiment" or "an alternative embodiment" mentioned twice or more in different portions of this specification does not necessarily refer to the same embodiment. Furthermore, the particular features, structures or characteristics may be combined properly in one or more embodiments of the present disclosure.

In addition, unless it is explicitly stated in claims, the order of the processing elements and sequences, use of numerals and letters, or use of other terms in the present specification are not intended to limit the order of the procedures and methods in the present specification. Although some embodiments of the invention that are currently considered useful are described by using various examples in the above disclosure, it should be understood that such details are merely for the purpose of illustration, and the appended claims are not limited to the disclosure of the embodiments. On the contrary, the claims are intended to cover all modifications and equivalent combinations in accordance with the spirit and scope of the embodiments of the present specification. For example, although the system components described above can be implemented by hardware devices, the system components can be implemented by only software solutions, for example, installing the described system on an existing service or a mobile device.

Similarly, it is worthwhile to note that, in order to simplify the disclosure of the present specification to facilitate understanding of one or more embodiments of the invention, a plurality of features are sometimes incorporated into one embodiment, one accompanying drawing, or the description thereof in the above description of the embodiments of the present specification. However, such a disclosure does not mean that the subject of the present specification requires more features than those in the claims. Actually, the features of an embodiment are fewer than all features of an individual embodiment disclosed above.

The entire contents of each patent, each patent application, each patent application publication, and other materials such as articles, books, specifications, publications, and documents cited in the present specification, excluding application history documents inconsistent with or conflicting with the contents of the present specification and documents (currently or subsequently appended to the present specification) that limit the broadest scope of the claims in the present specification, are hereby incorporated herein by reference. It is worthwhile to note that if the descriptions, definitions, and/or terms in the materials attached to the present specification are inconsistent with or in conflict with the contents of the present specification, the use of description, definitions, and/or terms in the present specification shall prevail.

Finally, it should be understood that the embodiments of the present specification are intended only to describe the principles of the embodiments of the present specification. Other variations may also fall within the scope of the present specification. Therefore, as examples instead of limitation, alternative configurations of the embodiments of the present specification can be considered to be consistent with the instructions of the present specification. Correspondingly, the embodiments of the present specification are not limited to the embodiments explicitly described and illustrated in the present specification.

What is claimed is:

1. A method for determining an intracranial hemodynamic parameter, comprising:

determining a three-dimensional vessel model based on CT angiographic data; and determining at least one of a boundary condition of each inlet or a boundary condition of each outlet in the three-dimensional vessel model based on CT perfusion imaging data and the CT angiographic data, wherein the CT perfusion imaging data are configured to determine at least one of a first total cerebral blood flow rate at all inlets, a cerebral blood flow rate at each outlet, and a second total cerebral blood flow rate at all outlets in the three-dimensional vessel model.

2. The method of claim 1, wherein the determining the at least one of the boundary condition of each inlet or the boundary condition of each outlet in the three-dimensional vessel model comprises determining the boundary condition of each inlet in the three-dimensional model, and the determining the boundary condition of each inlet in the three-dimensional model comprises:

determining angiographic information of each inlet in the three-dimensional vessel model based on the CT angiographic data, the angiographic information of each inlet comprising at least one of a first transluminal attenuation gradient (TAG) or a first CT value of the each inlet in the three-dimensional vessel model;

determining the first total cerebral blood flow rate based on the CT perfusion imaging data, the first total cerebral blood flow rate being a sum of cerebral blood flow rates at all the inlets in the three-dimensional vessel model; and determining the boundary condition of the each inlet in the three-dimensional vessel model based on the angiographic information of the each inlet and the first total cerebral blood flow rate.

3. The method of claim 2, wherein the determining the boundary condition of each inlet in the three-dimensional vessel model based on the angiographic information of the each inlet in the three-dimensional vessel model and the first total cerebral blood flow rate comprises one of the following:

determining a corrected flow rate at each inlet in the three-dimensional vessel model based on the first total cerebral blood flow rate and a ratio of the first TAG corresponding to the each inlet to a total inlet TAG, the total inlet TAG being a sum of the first TAGs of all the inlets in the three-dimensional vessel model;

determining a corrected flow rate at each inlet in the three-dimensional vessel model based on the first total cerebral blood flow rate and a ratio of the first CT value corresponding to the each inlet to a total CT value, the total CT value being a sum of the first CT values of all the inlets in the three-dimensional vessel model; and determining a corrected flow rate at each inlet in the three-dimensional vessel model based on the ratio of the first TAG corresponding to the each inlet to the total inlet TAG and the ratio of the first CT value corresponding to the each inlet to the total CT value and the first total cerebral blood flow rate.

4. The method of claim 1, wherein the determining the at least one of the boundary condition of each inlet or the boundary condition of each outlet in the three-dimensional vessel model comprises determining the boundary condition of each outlet in the three-dimensional model, and the determining the boundary condition of each outlet in the three-dimensional vessel model comprises:

determining the cerebral blood flow rate at each outlet in the three-dimensional vessel model and the second total cerebral blood flow rate at all the outlets based on the CT perfusion imaging data;

determining an outlet area, a second TAG, and a second CT value of each outlet in the three-dimensional vessel model based on the CT angiographic data; and determining the boundary condition of the each outlet in the three-dimensional vessel model based on one or more of the cerebral blood flow rate at the each outlet, the second total cerebral blood flow rate, the outlet area of the each outlet, the second TAG of the each outlet, and the second CT value of the each outlet.

5. The method of claim 4, wherein the determining the boundary condition of each outlet in the three-dimensional vessel model comprises:

determining an outlet resistance value of each outlet in the three-dimensional vessel model based on a total outlet resistance value and a ratio of the cerebral blood flow rate corresponding to the each outlet to the second total cerebral blood flow rate, the total outlet resistance value being a sum of the cerebral blood flow rates at all the outlets in the three-dimensional model; and determining an arterial viscous resistance and a peripheral resistance of the each outlet based on the outlet resistance value of the each outlet.

6. The method of claim 4, wherein the determining the boundary condition of each outlet in the three-dimensional vessel model comprises:

determining a compliance of the each outlet in the three-dimensional vessel model based on a total outlet compliance and the ratio of the cerebral blood flow rate corresponding to the each outlet to the second total cerebral blood flow rate, the total outlet compliance comprising a sum of compliances of all the outlets in the three-dimensional vessel model.

7. The method of claim 1, further comprising:

adjusting the three-dimensional vessel model based on adjustment parameters to obtain an adjusted three-dimensional vessel model; and determining a hemodynamic parameter for a specified region in the adjusted three-dimensional vessel model based on the adjusted three-dimensional vessel model and boundary conditions corresponding to the adjusted three-dimensional vessel model.

8. The method of claim 7, further comprising:
determining the boundary conditions corresponding to the adjusted three-dimensional vessel model based on the adjustment parameters.

9. A non-transitory computer-readable storage medium having computer instructions stored thereon, wherein, when executed by a processor, the computer instructions cause the processor to:
determine a three-dimensional vessel model based on CT angiography data; and
determine at least one of a boundary condition of each inlet or a boundary condition of each outlet in the three-dimensional vessel model based on CT perfusion imaging data and the CT angiography data, wherein the CT perfusion imaging data are configured to determine at least one of a first total cerebral blood flow rate at all inlets, a cerebral blood flow rate at each outlet, and a second total cerebral blood flow rate at all outlets in the three-dimensional vessel model.

10. The non-transitory computer-readable storage medium of claim 9, wherein
the instructions, when executed by the processor, cause the processor to:
determine angiographic information of each inlet in the three-dimensional vessel model based on the CT angiographic data, the angiographic information of each inlet comprising at least one of a first TAG or a first CT value of the each inlet in the three-dimensional vessel model;
determine the first total cerebral blood flow rate based on the CT perfusion imaging data, the first total cerebral blood flow rate being a sum of cerebral blood flow rates at all the inlets in the three-dimensional vessel model; and
determine the boundary condition of the each inlet in the three-dimensional vessel model based on the angiographic information of the each inlet and the first total cerebral blood flow rate.

11. The non-transitory computer-readable storage medium of claim 10, wherein
the instructions, when executed by the processor, cause the processor to perform one of the following:
determining a corrected flow rate at each inlet in the three-dimensional vessel model based on the first total cerebral blood flow rate and a ratio of the first TAG corresponding to the each inlet to a total inlet TAG, the total inlet TAG being a sum of the first TAGs of all the inlets in the three-dimensional vessel model;
determining a corrected flow rate at each inlet in the three-dimensional vessel model based on the first total cerebral blood flow rate and a ratio of the first CT value corresponding to the each inlet to a total CT value, the total CT value being a sum of the first CT values of all the inlets in the three-dimensional vessel model; or
determining a corrected flow rate at each inlet in the three-dimensional vessel model based on the ratio of the first TAG corresponding to the each inlet to the total inlet TAG and the ratio of the first CT value corresponding to the each inlet to the total CT value and the first total cerebral blood flow rate.

12. The non-transitory computer-readable storage medium of claim 9, wherein
the instructions, when executed by the processor, cause the processor to:
determine the cerebral blood flow rate at each outlet in the three-dimensional vessel model and the second total cerebral blood flow rate at all the outlets based on the CT perfusion imaging data;
determine an outlet area, a second TAG, and a second CT value of each outlet in the three-dimensional vessel model based on the CT angiographic data; and
determine the boundary condition of the each outlet in the three-dimensional vessel model based on one or more of the cerebral blood flow rate at the each outlet, the second total cerebral blood flow rate, the outlet area of the each outlet, the second TAG of the each outlet, and the second CT value of the each outlet.

13. The non-transitory computer-readable storage medium of claim 12, wherein
the instructions, when executed by the processor, cause the processor to:
determine an outlet resistance value of each outlet in the three-dimensional vessel model based on a total outlet resistance value and a ratio of the cerebral blood flow rate corresponding to the each outlet to the second total cerebral blood flow rate, the total outlet resistance value being a sum of the cerebral blood flow rates at all the outlets in the three-dimensional model; and
determine an arterial viscous resistance and a peripheral resistance of the each outlet based on the outlet resistance value of the each outlet.

14. The non-transitory computer-readable storage medium of claim 12, wherein
the instructions, when executed by the processor, cause the processor to:
determine a compliance of the each outlet in the three-dimensional vessel model based on a total outlet compliance and the ratio of the cerebral blood flow rate corresponding to the each outlet to the second total cerebral blood flow rate, the total outlet compliance comprising a sum of compliances of all the outlets in the three-dimensional vessel model.

15. The non-transitory computer-readable storage medium of claim 9, wherein
the instructions, when executed by the processor, cause the processor to:
adjust the three-dimensional vessel model based on adjustment parameters to obtain an adjusted three-dimensional vessel model; and
determine a hemodynamic parameter for a specified region in the adjusted three-dimensional vessel model based on the adjusted three-dimensional vessel model and boundary conditions corresponding to the adjusted three-dimensional vessel model.

16. The non-transitory computer-readable storage medium of claim 15, wherein
the instructions, when executed by the processor, cause the processor to:
determine the boundary conditions corresponding to the adjusted three-dimensional vessel model based on the adjustment parameters.

17. A device for determining an intracranial hemodynamic parameter, comprising:
a processor; and
a memory including computer instructions stored thereon which, when executed by the processor, causes the processor to:
determine a three-dimensional vessel model based on CT angiography data; and
determine at least one of a boundary condition of each inlet or a boundary condition of each outlet in the three-dimensional vessel model based on CT perfusion imaging data and the CT angiography data, wherein the CT perfusion imaging data are configured to determine at least one of a first total cerebral blood flow rate at all inlets, a cerebral blood flow rate at each outlet, and a second total cerebral blood flow rate at all outlets in the three-dimensional vessel model.

18. The device of claim 17, wherein the instructions, when executed by the processor, cause the processor to:

determine angiographic information of each inlet in the three-dimensional vessel model based on the CT angiographic data, the angiographic information of each inlet comprising at least one of a first TAG or a first CT value of the each inlet in the three-dimensional vessel model;

determine the first total cerebral blood flow rate based on the CT perfusion imaging data, the first total cerebral blood flow rate being a sum of cerebral blood flow rates at all the inlets in the three-dimensional vessel model; and determine the boundary condition of the each inlet in the three-dimensional vessel model based on the angiographic information of the each inlet and the first total cerebral blood flow rate.

19. The device of claim 17, wherein the instructions, when executed by the processor, cause the processor to:

determine the cerebral blood flow rate at each outlet in the three-dimensional vessel model and the second total cerebral blood flow rate at all the outlets based on the CT perfusion imaging data;

determine an outlet area, a second TAG, and a second CT value of each outlet in the three-dimensional vessel model based on the CT angiographic data; and determine the boundary condition of the each outlet in the three-dimensional vessel model based on one or more of the cerebral blood flow rate at the each outlet, the second total cerebral blood flow rate, the outlet area of the each outlet, the second TAG of the each outlet, and the second CT value of the each outlet.

20. The device of claim 19, wherein the instructions, when executed by the processor, cause the processor to:

the instructions, when executed by the processor, cause the processor to:

determine an outlet resistance value of each outlet in the three-dimensional vessel model based on a total outlet resistance value and a ratio of the cerebral blood flow rate corresponding to the each outlet to the second total cerebral blood flow rate, the total outlet resistance value being a sum of the cerebral blood flow rates at all the outlets in the three-dimensional model; and determine an arterial viscous resistance and a peripheral resistance of the each outlet based on the outlet resistance value of the each outlet.

* * * * *